United States Patent [19]

Shah et al.

[11] Patent Number: 5,527,271
[45] Date of Patent: Jun. 18, 1996

[54] THERMOPLASTIC HYDROGEL IMPREGNATED COMPOSITE MATERIAL

[75] Inventors: Kishore R. Shah, Bridgewater; Agis Kydonieus, Kendall Park; Khosrow Jamshidi, Princeton; Stefanie C. Decker, Franklin Park; Tak-lung Chang, Skillman, all of N.J.

[73] Assignee: Bristol-Myers Squibb Co., Skillman, N.J.

[21] Appl. No.: 220,350

[22] Filed: Mar. 30, 1994

[51] Int. Cl.$^6$ ..................................................... A61F 13/00
[52] U.S. Cl. .............................. 602/48; 604/368; 602/44
[58] Field of Search ................................. 602/43, 44, 46, 602/48, 52, 41; 604/368, 367, 369, 374

[56] References Cited

U.S. PATENT DOCUMENTS

| | | | |
|---|---|---|---|
| 3,425,412 | 2/1969 | Pope | 128/156 |
| 4,297,410 | 10/1981 | Tsuchiya et al. | 428/283 |
| 4,338,371 | 7/1982 | Dawn et al. | 428/283 |
| 4,413,995 | 11/1983 | Korpman. | |
| 4,513,739 | 4/1985 | Johns | 128/156 |
| 4,535,098 | 8/1985 | Evani et al. . | |
| 4,654,039 | 3/1987 | Brandt et al. . | |
| 4,724,114 | 2/1988 | McFarland et al. | 264/510 |
| 4,842,593 | 1/1989 | Jordan et al. | 604/360 |
| 4,889,530 | 12/1989 | Smith et al. . | |
| 4,909,244 | 3/1990 | Quarfoot et al. . | |
| 4,929,577 | 5/1990 | Cornell . | |
| 4,930,500 | 6/1990 | Morgan . | |
| 4,977,892 | 12/1990 | Ewall . | |
| 4,979,946 | 12/1990 | Gilman . | |
| 4,985,298 | 1/1991 | Buckley et al. . | |
| 5,002,792 | 3/1991 | Vegoe | 427/2 |
| 5,071,681 | 12/1991 | Manning et al. . | |
| 5,076,265 | 12/1991 | Wokalek . | |
| 5,098,775 | 3/1992 | Harada et al. . | |
| 5,106,629 | 4/1992 | Cartmell et al. . | |
| 5,115,801 | 5/1992 | Cartmell et al. . | |
| 5,147,343 | 9/1992 | Kellenberger . | |
| 5,149,333 | 9/1992 | Sasse . | |
| 5,156,601 | 10/1992 | Lorenz et al. . | |
| 5,160,328 | 11/1992 | Cartmell et al. . | |
| 5,204,110 | 4/1993 | Cartmell et al. . | |
| 5,219,325 | 6/1993 | Hennink et al. . | |
| 5,277,915 | 1/1994 | Provonchee et al. . | |
| 5,306,504 | 4/1994 | Lorenz . | |
| 5,352,480 | 10/1994 | Hansen et al. | 427/202 |

Primary Examiner—Randall L. Green
Assistant Examiner—Chalin Smith
Attorney, Agent, or Firm—Theodore R. Furman, Jr.

[57] ABSTRACT

A composite material for wound dressings having a fibrous wound-contacting substrate, such as cotton gauze, impregnated with a thermoplastic hydrogel forming polymer and methods of making the same.

19 Claims, No Drawings

THERMOPLASTIC HYDROGEL IMPREGNATED COMPOSITE MATERIAL

FIELD OF THE INVENTION

The present invention is directed to a composite material suitable for application as a wound dressing. The composite material includes a fibrous wound-contacting substrate, such as a cotton gauze, impregnated with a thermoplastic hydrogel forming polymer. The composite material is highly absorbent and does not stick to the wound surface.

BACKGROUND OF THE INVENTION

Conventional materials for use as wound dressings, such as cotton gauze, suffer from a number of disadvantages. For example, cotton gauze tends to stick to the wound during the healing process. Removal of the wound dressing under these circumstances destroys tissue and is uncomfortable for the patient. To reduce sticking and optimize wound healing, the wound dressing must be replaced often.

Another disadvantage of using cotton gauze in wound dressings arises from the construction of the gauze material. Cotton gauze is manufactured from twisted cotton fiber which is cleaned, bleached and sterilized. During the cleaning and bleaching process, the thread is exposed to chemical treatments and becomes associated with leftover starch, proteins, casein and resins. These materials, plus small fibers or lint, often disassociate from the cotton gauze and contaminate the wound. In some cases, particularly during surgery, serious infections can result.

Efforts have been made to overcome the disadvantages associated with gauze-type wound dressings by coating or impregnating the gauze material. Romano Cali, U.S. Pat. No. 4,748,976 discloses a wound dressing in which a cotton fabric is impregnated with a cosmetic preparation held in an oil or a grease medium. Nigel J. Brassington et al., U.S. Pat. No. 4,838,253 disclose a wound dressing comprised of a cotton gauze coated with a tacky silicone gel or a non-tacky silicone elastomer.

Paul F. Hermann et al., U.S. Pat. No. 5,135,472 disclose a composite gauze material coated with a hydrophilic polymer. The polymer is stated to bind with the hydroxyl groups of the gauze material. Such polymers include a polyurethane foam prepolymer, and polymers of ethylene oxide, carboxymethyl cellulose or polyvinylpyrrolidone.

Despite these efforts there is a continuing need to develop composite materials for use as wound dressings which are highly absorbent, do not stick to the wound and reduce or eliminate infiltration of fibers and by-products of manufacture into the wound.

SUMMARY OF THE INVENTION

The present invention is directed to a composite material particularly suited as a wound dressing. The composite material is comprised of a fibrous wound-contacting substrate, the most common example of which is cotton gauze. The substrate is impregnated with a layer of a thermoplastic hydrogel forming polymer (hereinafter "the hydrogel polymer"). Such polymers include A-B-A block copolymers, multiblock copolymers, graft copolymers and polymer blends each incorporating a hydrophilic component and a hydrophobic component. The hydrogel polymer exhibits microphase separation of the hydrophobic component which makes the hydrogel polymer water insoluble, yet water-swellable, and therefore highly absorbent.

The substrate/hydrogel polymer composite resulting from impregnation of the substrate with the hydrogel polymer is initially dry. Upon the uptake of exudate from the wound, the dry composite becomes slippery or "slimy" and thereby does not entrap tissue so that the wound dressing does not stick to the wound during healing. Consequently upon removal of the wound dressing, there is minimal or no injury to the healing tissue. Further, due to increased absorptive capacity, the composite material of the present invention may be retained on the wound for longer periods of time than conventional cotton gauze. Fewer changes of the wound dressing reduces material costs and reduces the time needed by medical personnel to administer to a patient's wound.

DETAILED DESCRIPTION OF THE INVENTION

The present invention is directed to a composite material adapted for use as a wound dressing in which a fibrous wound-contacting substrate, impregnated with a thermoplastic hydrogel-forming polymer, is placed in direct contact with an open wound. Examples of such substrates include pure cotton fabric, cotton gauze, and open weave cellulose fiber materials such as those disclosed in Romano Cali, U.S. Pat. No. 4,748,976; Nigel J. Brassington et al., U.S. Pat. No. 4,838,253; Paul F. Hermann et al., U.S. Pat. No. 5,135,472; and Richard B. Ponder et al., "Gauzes and Related Dressings", *Ostomy/Wound Management*, Vol. 39, No. 5, pp. 48–60 (June, 1993), each of which is incorporated herein by reference. Synthetic materials such as rayon, rayon/polyester blends, Dacron and the like may also be used.

The wound-contacting substrate is impregnated with the hydrogel polymer. The hydrogel polymers having application in the present invention include A-B-A block copolymers, multiblock copolymers, graft copolymers and polymer blends each incorporating a hydrophilic and a hydrophobic component. The hydrogel polymers which are particularly advantageous in the present invention are those exhibiting microphase separation with a hydrophilic/hydrophobic domain system.

Such hydrogel polymers are thermoplastic. Accordingly, they are soluble in conventional organic solvents and soften upon the application of heat. The hydrogel polymers are distinguished from thermosetting polymers which are insoluble in organic solvents and do not melt upon heating. The hydrogel polymers employed in the present invention may therefore be prepared separately, purified, and then impregnated into the substrate. Thermoplastic hydrogel polymers for use in the present invention are disclosed in, for example, "Water-Soluble Polymers", K. R. Shah in S. W. Shalaby et al., *ACS Symposium Series*, Vol. 67, Chapter 30, pp. 469–483 (1991), incorporated herein by reference.

The morphology of the hydrogel polymers is characterized by a hydrophilic or water soluble continuous phase and a hydrophobic or water insoluble dispersed phase, which prevents the continuous phase from dissolving in water. Thus, when the hydrogel polymer is placed in an aqueous environment, it absorbs water and swells to an equilibrium volume, but does not dissolve in water. More specifically, the hydrogel polymers have an equilibrium water content, defined as the percentage by weight of water absorbed, based on the weight of the hydrated sample, of up to about 99%, typically from about 40 to 99%.

The polymer systems which exhibit hydrophilic-hydrophobic domains include, but are not limited to (a) A-B-A block copolymers,.(b) multiblock copolymers, (c) graft copolymers and (d) polymer blends, each having a hydrophilic and a hydrophobic component.

The A-B-A type block copolymers are those wherein the A block is hydrophobic and the B block is hydrophilic. Examples of hydrophobic blocks include polystyrene, poly(methyl methacrylate), polyacrylonitrile, polyesters, polyamides, and the like. Examples of hydrophilic blocks include polyethylene oxide, poly(hydroxyalkyl methacrylate) and derivatives thereof, polyacrylamide, poly(N-vinyl lactam), polyacrylic acid, and the like. Some of the polymeric compositions which fall under this category include: copolymers of styrene and 2-hydroxyethyl methacrylate reported by T. Okano, et al.; *J. Appl. Polym. Sci.*, Vol. 22, p. 369 (1978) and *J. Biomed. Mat. Research*, Vol. 15, p. 393 (1981), each of which is incorporated herein by reference; triblock copolymers based on polyethylene oxide and lactic acid and trimethylene carbonate copolyester as disclosed in L. Rosati et al., *Polym. Mat. Sci. & Eng., Am. Chem. Soc., Preprints*, Vol. 59, p. 516 (1988); triblock copolymer of poly(hydroxyalkyl L-glutamine) and polyethylene oxide as disclosed in *Am. Chem. Soc., Symp., Ser.*, No. 520 (1992). Methods of preparing A-B-A type block copolymers for use in the present invention are also disclosed in these publications, each of which is incorporated herein by reference.

The multiblock copolymers have alternating sequences of hydrophilic and hydrophobic polymeric blocks as described above for the A-B-A type block copolymers. Examples of these copolymers include copolymers of polyacrylonitrile and hydrophilic derivatives of acrylic acid as disclosed in V. A. Stoy et al., U.S. Pat. No. 4,095,877 and V. A. Stoy, U.S. Pat. No. 4,369,294, and polyethylene oxide/lactic acid copolymers as disclosed in D. Cohn, et al., *J. Biomed. Mat Res.*, Vol. 22, p. 993 (1988). Methods of preparation of the multiblock copolymers for use in the present invention are also disclosed in the publications, each of which is incorporated herein by reference.

The graft copolymers comprise hydrophilic main chain polymer and hydrophobic polymeric grafts. Hydrophobic and hydrophilic structures for the graft copolymers are as described above for the A-B-A type block copolymers. Examples of such graft copolymers include poly(N,N-dimethylacrylamide-g-styrene) as disclosed in R. Milkovich et al., U.S. Pat. No. 4,085,168; and poly(2,3-dihydroxypropyl methacrylate-g-styrene) as disclosed in T. Tsukahara, et al., *Polym. J.*, Vol. 19, p. 1033 (1987). Methods of preparation of the graft copolymers for use in the present invention are also disclosed in the publications, each of which is incorporated herein by reference.

The polymer blends are preferably blends of two polymers, one of which is a homopolymer or a copolymer of an N-vinyl lactam and the other is an acrylic copolymer containing a small proportion of acidic groups as disclosed in K. Shah, U.S. Pat. No. 4,300,820, incorporated herein by reference which also discloses methods of forming the polymer blends.

The copolymers including A-B-A block, multiblock and graft copolymers and the polymer blends employed in the present invention may be formed as a solution or may be melt processed through an extruder to impregnate the hydrogel polymer into the substrate.

For example, a graft copolymer of N,N,dimethylacrylamide and the polystyrene-based macromonomer may be prepared by free radical initiated solution copolymerization. The starting materials are reacted in the presence of a polymerization solvent, such as ethyl acetate, ethanol, methyl ethyl ketone, acetone, tetrahydrofuran, mixtures thereof and the like, and a polymerization catalyst (e.g. asobisisobutyronitrile) at a reaction temperature in the range of up to about 80° C.

The resulting solution containing the copolymer is then optionally purified to remove unreacted monomer and other impurities. For example, the copolymer solution may be precipitated with a non-solvent, such as an ether compound, in particular diethyl ether, at a weight ratio of about 1:1 to 1:10, preferably about 1:2. The resulting precipitated copolymer is separated, and dried and then reconstituted in solution by adding additional solvent.

The copolymer containing solution may be combined with a conventional plasticizer such as polyethylene glycol (e.g. PEG- 400), glycerine, mixtures thereof and the like to form a solution for impregnating the substrate.

The solution typically contains up to 40% by weight, preferably from about 2 to 20% by weight, of the hydrogel polymer. The hydrogel polymer may optionally contain up to about 60% by weight, preferably form about 15 to 60% by weight of the plasticizer based on the weight of the plasticized hydrogel polymer. The balance of the solution is comprised of an organic solvent, typically from about 60 to 96% by weight of the solution.

The copolymer containing solution is applied to the wound-contacting substrate in any manner capable of uniformly impregnating the substrate. Dipping and spraying are two conventional methods for impregnating the solution although dipping is preferred. In this method, the wound-contacting substrate is dipped into a bath containing the solution. The impregnated substrate is then removed from the bath and allowed to dry. During the drying step, the solvent evaporates leaving the plasticized thermoplastic hydrogel on the substrate.

Alternatively, the hydrogel polymer, optionally with a plasticizer, may be melt processed through an extruder to impregnate the hydrogel polymer into the substrate. The hydrogel polymer in the form of a dry powder is placed into an extruder and heated. The melted hydrogel polymer is then formed into a sheet atop the substrate. The composite is then compressed until the hydrogel polymer impregnates the substrate.

The extent to which the hydrogel polymer is impregnated into the substrate is selected depending on the desired absorption capabilities of the wound dressing. Generally, the greater the amount of the hydrogel polymer impregnated, the greater the absorption capability of the wound dressing and the longer the wound dressing may be retained on the wound. The extent of impregnation is related to the dry weight of the applied hydrogel polymer per unit weight of the wound-contacting substrate. For most standard substrates, (e.g. cotton gauze) the dry weight of the impregnated polymer is in the range of from about 50 to 500% by weight of the cotton gauze, preferably from about 60 to 150% by weight.

The composite material of the present invention can absorb moisture up to about 15 times its weight, depending on the relative weight of the hydrogel polymer, without being dissolved away from the wound-contacting substrate. The hydrogel polymer is essentially in a dry state on the wound-contacting substrate and becomes slippery as it absorbs moisture. Slippery or lubricous substrates serve the function of preventing adhesion of the substrate to the tissue of the wound. When the substrate is removed, the material comprising the substrate such as gauze is easily separated from the tissue without damaging the wound or inflicting pain on the patient. The impregnation of a gauze like fibrous wound contacting substrate in accordance with the invention prevents shedding of lint and other particulate matter into the wound.

In accordance with another aspect of the claimed invention, the composite material containing the hydrogel polymer impregnated therein may have optionally thereon a material which improves handling or lubricity of the composite material. The preferred type of material for this purpose is a water-soluble biocompatible material in the form of fine particles (e.g. a powder). Such materials include gelatin, pectin, dextran and sodium carboxymethylcellulose. The amount of such materials should be sufficient to eliminate any residual tackiness of the composite material.

The composite material as described above may be incorporated into a variety of wound dressings including top dressings for superficial-type wounds as well as packing dressings for chronic and traumatic wounds. Examples of the former type of wound dressings are disclosed, for example, in U.S. Pat. Nos. 3,425,412 and 4,513,739 and U.S. Patents disclosed therein, each of which is incorporated herein by reference. Common wound care products are also disclosed in Richard B. Ponder, et al. publication previously mentioned.

Composite materials in accordance with the present invention absorb significantly more exudate from a wound than conventional uncoated gauze-type materials. By way of example, if a conventional wound dressing required replacement 3 to 4 times over the course of an eight hour nurses shift, a wound dressing of the present invention may require only a single replacement.

EXAMPLE 1

67 ml of ethyl acetate was charged into a four-mouth round bottom flask. 32.175g of N,N-dimethylacrylamide and 0.825g of polystryene methacrylate macromonomer having a number average molecular weight of 13,000 (manufactured by Sartomer) were added to the flask. 0.033g of azobisisobutyronitrile dissolved in 2.0 ml of ethyl acetate was slowly added to the mixture under constant stirring until a completely clear mixture was obtained.

The flask was placed in an ethylene glycol bath maintained at 50° C. for 60 minutes. The bath temperature was gradually raised to 80° C. over 15 minutes and the contents of the flask continuously mixed over the next 120 minutes. Thereafter, the reaction was terminated by removing the flask from the bath and allowing the reaction mixture to cool.

The resulting solution containing the graft copolymer composed of 2.5% by weight of polystyrene methacrylate was combined with 200 ml of diethyl ether, whereupon the graft copolymer precipitated. The supernatant liquid was decanted and the graft copolymer residue washed with diethyl ether until the washings were completely clear.

The purified graft copolymer was combined with 300 ml of ethyl acetate and 27g of polyethylene glycol (PEG-400 Aldrich Chemicals) and stirred until a homogenous solution was obtained. The solution was cast over folded silicone coated release papers and allowed to dry overnight. The sheets were then placed in a vacuum oven and dried overnight at room temperature followed by drying at 50° C. for at least 5 hours.

The copolymer sheet was immersed in water for 24 hours. The fully hydrated graft copolymer was removed from the liquid, weighed, dried at 50° C. for 24 hours and then reweighed. The equilibrium water concentration (EWC) of the hydrated copolymer was 97% as shown in Table 1.

TABLE 1

| EXAMPLE | *AMOUNT OF MACROMONOMER IN THE GRAFT COPOLYMER (% BY WEIGHT) | EWC (%)[1] |
|---------|---------|---------|
| 1 | 2.5 | 97 |
| 2 | 5.0 | 95 |
| 3 | 10.0 | 91 |
| 4 | 20.0 | 75 |
| 5 | 30.0 | 63 |

[1] - Percentage by weight of water absorbed based on the weight of the hydrated sample.

EXAMPLES 2–5

Example 1 was repeated for each of Examples 2–5 except that the amount of the polystyrene methacrylate macromonomer in the graft copolymer was increased to 5.0, 10.0, 20.0 and 30.0% by weight, respectively. The results are shown in Table 1.

As shown in Table 1 each of Examples 1–5 show significant water absorption. It is further shown that the amount of water absorption increases as the amount of the polystyrene methacrylate macromonomer in the graft copolymer decreases.

EXAMPLES 6–8

20.0 parts by weight of the hydrogel polymer formed in accordance with the method of Example 3 was dissolved in 63.6 parts by weight of acetone containing 16.4 parts by weight of PEG-400 to obtain a clear hydrogel solution.

A woven type I gauze was dipped into the hydrogel solution for a few seconds. The residual solution was removed by passing the gauze through a pair of rollers. The gauze was heated in an oven at 120° C. for three minutes to evaporate the solvent.

A 2"×4" sample of the gauze (Example 6) was placed on a piece of wet sponge in a chamber having a temperature of 40° C. and a relative humidity of 75%. The weight of the sample was measured every 5 minutes during the first 30 minutes and every 30 minutes for the next two hours until saturation.

The amount of water absorbed by the sample was calculated as follows:

$$\frac{\text{water absorption}}{\text{at designated time}} = \frac{\text{wt(time)} - \text{wt1}}{\text{unit area}}$$

wt (time)=weight of the sample at the designated time
wt1=dry weight of the sample before being placed on the sponge Two additional samples (Examples 7 and 8) were prepared and tested in the same manner as Example 6 except that the dipping and drying process was repeated to increase the amount of the hydrogel polymer impregnated in the gauze material as indicated in Table 2.

TABLE 2

| EXAMPLE | HYDROGEL POLYMER WEIGHT[2] | AMOUNT OF PEG[3] | WATER ABSORPTION G/M$^2$ 5 MIN | 25 MIN. |
| --- | --- | --- | --- | --- |
| 6 | 30% | 45% | 61 | 63 |
| 7 | 53% | 45% | 90 | 100 |
| 8 | 63% | 45% | 137 | 128 |

[2] - Based on the weight of the non-impregnated gauze.
[3] - Based on the combined weight of the hydrogel polymer and PEG.

As shown in Table 2, Examples 6–8 provide significant water absorption in just 5 minutes and retain the absorbed water. Table 2 further shows that increasing the weight of the hydrogel polymer increases the amount of water absorption of the gauze material.

EXAMPLE 9

A sample of a hydrogel polymer impregnated gauze was prepared in the same manner as Example 6. After drying of the hydrogel polymer, a small amount of sodium carboxymethylcellulose powder (6–30 mg/in$^2$) was sprinkled onto both sides of the gauze.

The thus treated sample was tested for water absorption in the same manner as Example 6. The test results showed that the sample (Example 9) exhibited a slight increase in the rate of water absorption over Examples 6–8. There was also observed a reduction in the adhesiveness of the surface of the gauze material.

COMPARATIVE EXAMPLE

The same type of gauze material employed in Examples 1–8 without the hydrogel polymer of the present invention was tested for water absorbency in the same manner as Examples 1–8. After 5 minutes, the amount of water absorbed was about 37 g/m$^2$. After 25 minutes, the amount of water absorbed decreased to about 27 g/m$^2$.

As shown in the Examples, the water absorbing capability of wound dressings impregranted with the hydrogel polymer in accordance with the present invention significantly exceeds the water absorbing capability of conventional gauze. In addition, the wound dressings of the present invention do not stick to the wound because, once exudate is absorbed, the wound dressing becomes slippery and does not adhere to tissue during the wound healing process.

What is claimed is:

1. A composite material for a wound dressing comprising:
   (a) a fibrous wound-contacting substrate; and
   (b) a thermoplastic hydrogel forming polymer selected from the group consisting of A—B—A block copolymers, multiblock copolymers, graft copolymers and polymer blends each incorporating a hydrophilic component and a hydrophobic component impregnated into said substrate.

2. The composite material of claim 1 wherein the thermoplastic hydrogel forming polymer exhibits microphase separation having a hydrophilic/hydrophobic domain polymer system.

3. The composite material of claim 1 wherein the thermoplastic hydrogel forming polymer has an equilibrium water content in the range of from about 40 to 99%.

4. The composite material of claim 1, wherein the A-B-A type block copolymers have hydrophobic blocks selected from the group consisting of polystyrene, poly(methyl methacrylate), polyacrylonitrile, polyesters and polyamides, and the hydrophilic blocks are selected from the group consisting of polyethylene oxide, poly(hydroxyalkyl methacrylate), and derivatives thereof, polyacrylamide, poly(N-vinyl lactam) and polyacrylic acid.

5. The composite material of claim 1 wherein the multiblock copolymers are selected from the group consisting of copolymers of polyacrylanitrile and hydrophilic derivatives of acrylic acid and copolymers of polyethylene oxide and lactic acid.

6. The composite material of claim 1 wherein the polymer blend is selected from the group consisting of a homopolymer or a copolymer of N-vinyl lactam and an acrylic copolymer containing a small proportion of acidic groups.

7. The composite material of claim 1 wherein the thermoplastic hydrogel forming polymer is present in an amount of from about 50 to 500% by weight based on the weight of the wound-contacting substrate.

8. The composite material of claim 1 wherein the wound-contacting substrate is cotton gauze.

9. The composite material of claim 1 wherein the thermoplastic hydrogel film forming polymer contains up to about 60% by weight of a plasticizer.

10. The composite material of claim 1 further comprising a water-soluble biocompatible material in the form of fine particles placed on the thermoplastic hydrogel forming polymer.

11. The composite material of claim 10 wherein the fine particle material is selected from the group consisting of gelatin, pectin, dextran and carboxymethylcellulose.

12. The composite material of claim 1 wherein the graft copolymers are selected from the group consisting of poly(N,N-dimethylacrylamide-g-styrene) and poly (2,3 -dihydroxypropyl methacrylate-g-styrene).

13. The composite material of claim 12 wherein the thermoplastic hydrogel forming polymer is present in an amount of from about 60 to 150% by weight based on the weight of the wound-contacting substrate.

14. A method of forming a composite material for a wound dressing comprising:
   (a) forming a solution containing a thermoplastic hydrogel film forming polymer;
   (b) applying the solution to a fibrous wound-contacting substrate; and
   (c) drying the solution on the fibrous wound-contacting substrate to said composite material.

15. The method of claim 14 wherein the solution further comprises a solvent and a plasticizer.

16. The method of claim 15 wherein the solution contains up to 40% by weight of the thermoplastic hydrogel forming polymer.

17. The method of claim 14 wherein the amount of the plasticizer is up to 60% by weight of the total weight of the thermoplastic hydrogel polymer and the plasticizer.

18. A method of forming a composite material for a wound dressing comprising:
   (a) melt processing the thermoplastic hydrogel polymer through an extruder;
   (b) placing the extruded thermoplastic hydrogel polymer onto a substrate; and
   (c) applying pressure to the polymer and substrate to form the composite material.

19. The method of claim 18 wherein the thermoplastic hydrogel polymer further comprises a plasticizer.

* * * * *